United States Patent [19]
Lasner

[11] Patent Number: 5,492,442
[45] Date of Patent: Feb. 20, 1996

[54] BONE SCREW WITH IMPROVED THREADS

[75] Inventor: Jeffrey I. Lasner, Purchase, N.Y.

[73] Assignee: National Medical Specialty, Inc., Youngwood, Pa.

[21] Appl. No.: 201,018

[22] Filed: Feb. 24, 1994

Related U.S. Application Data

[63] Continuation-in-part of Ser. No. 90,550, Jul. 13, 1993, Pat. No. 5,417,533, which is a continuation of Ser. No. 886,380, May 21, 1992, Pat. No. 5,226,766, which is a continuation of Ser. No. 618,500, Nov. 27, 1990, Pat. No. 5,120,171.

[51] Int. Cl.⁶ ............................. F16B 35/04; F16B 39/30
[52] U.S. Cl. ........................... 411/426; 411/411; 411/308; 411/310; 606/73
[58] Field of Search .................... 411/308–311, 386, 411/387, 411, 424, 426; 606/65, 73

[56] References Cited

U.S. PATENT DOCUMENTS

| | | |
|---|---|---|
| Re. 28,111 | 8/1974 | Laverty . |
| D. 51,291 | 9/1917 | Vorel . |
| D. 52,511 | 10/1918 | Groh . |
| 74,489 | 2/1868 | Bidwell . |
| 197,933 | 12/1877 | Harvey . |
| 1,891,895 | 12/1932 | Nagel . |
| 1,980,093 | 11/1934 | Rosenberg . |
| 2,005,672 | 6/1935 | Chaffee . |
| 2,570,465 | 10/1951 | Lundholm . |
| 2,696,817 | 12/1954 | Prevo . |
| 2,702,543 | 2/1955 | Pugh et al. . |
| 2,772,676 | 12/1956 | Pohl . |
| 2,822,418 | 2/1958 | Dinnick . |
| 3,109,691 | 11/1963 | Burkhardt . |
| 3,233,500 | 2/1966 | de Vellier . |
| 3,466,748 | 9/1969 | Christensen . |
| 3,492,906 | 2/1970 | Hauser . |
| 3,703,843 | 11/1972 | Laverty . |
| 3,861,269 | 1/1975 | Laverty . |
| 4,175,555 | 11/1979 | Herbert . |
| 4,177,524 | 12/1979 | Grell et al. . |
| 4,261,351 | 4/1981 | Scherfel . |
| 4,463,753 | 8/1984 | Gustilo . |
| 4,569,338 | 2/1986 | Edwards . |
| 4,640,271 | 2/1987 | Lower . |
| 4,756,653 | 7/1988 | Berger . |
| 4,791,918 | 12/1988 | von Hasselbach . |
| 4,870,957 | 10/1989 | Goble et al. . |
| 4,892,429 | 1/1990 | Giannuzzi . |

FOREIGN PATENT DOCUMENTS

| | | |
|---|---|---|
| 282789 | 9/1988 | European Pat. Off. . |
| 77837 | 6/1918 | Switzerland . |
| 2090745 | 7/1982 | United Kingdom . |
| 2033755 | 5/1990 | United Kingdom . |

OTHER PUBLICATIONS

SOFAMOR "The Spine Specialist" promotional material and photocopy of a bone screw.
"Youngstown Sliding Lag Screw and Plate" News Release dated Sep. 1, 1988.
"Dr. Virgin Hip Fixation Screw", *Surgical Equipment*, vol. 7, No. 4, pp. 14 and 15, Jul., 1940.

*Primary Examiner*—Neill R. Wilson
*Attorney, Agent, or Firm*—Nixon & Vanderhye

[57] ABSTRACT

A bone screw having a helical thread with a constant outside diameter and curling around a tapered core. The fine screw tip and thread at the tip of the screw can be inserted into a bone with minimal tearing or cracking of the bone. The thicker core just below the screw head increases the screw's ability to withstand compressive and distractive loads. The core is thickest just below the head because it is at that point on the screw that the fulcrum loads are greatest.

5 Claims, 3 Drawing Sheets

FIG. 8
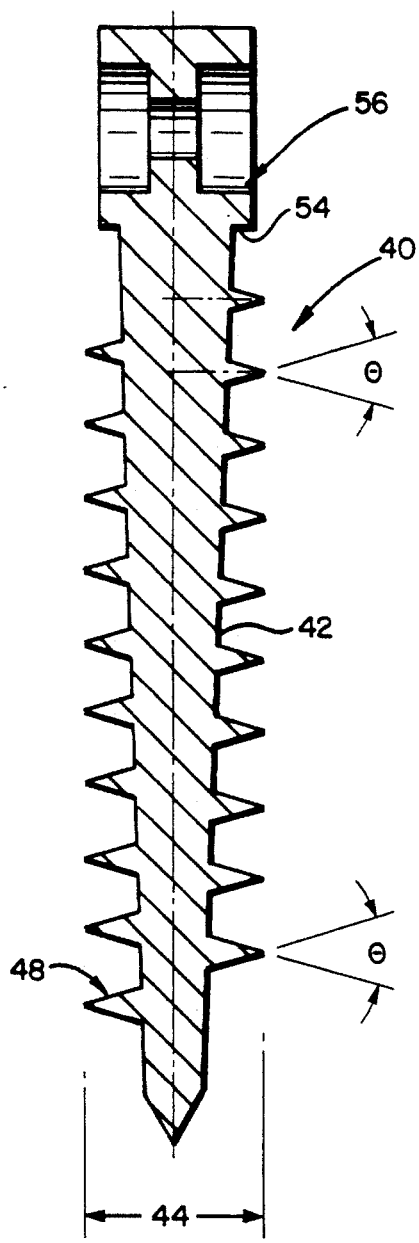
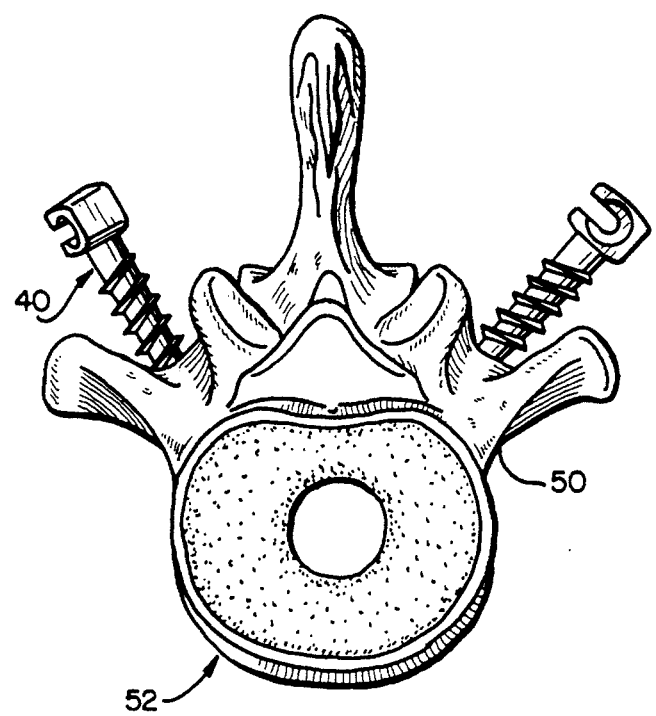
FIG. 9

BONE SCREW WITH IMPROVED THREADS

This application is a continuation-in-part of application Ser. No. 08/040,550, filed Jul. 13, 1993, now U.S. Pat. No. 5,417,533, issed May 23, 1995, which is a continuation of application Ser. No. 07/886,380, filed May 21, 1992, now U.S Pat. No. 5,226,766, issued Jul. 13, 1993 which is a continuation of application Ser. No. 07/618,500, filed Nov. 27, 1990, now U.S. Pat. No. 5,120,171, issued Jun. 23, 1992.

FIELD OF THE INVENTION

This invention relates to a screw having a tapered core and helical threads having a constant outside diameter. The screw has proven surprisingly useful in certain medical applications as a bone screw.

BACKGROUND AND SUMMARY OF THE INVENTION

Although bone screws are known, the threads on bone screws have been given scant attention. The threads anchor the screw into the bone. The treads keep the screw from being axially pulled out of the bone. The threads cut a helical path into the bone as the screw rotates into the bone. Given the importance of the screw threads, it is surprising that there was no reference known to me on the design of screw thread shapes.

There are many variable aspects of thread shape. The thread can have a sharp or blunt apex. The pitch of the thread can be varied. A shallow thread pitch provides many turns around the screw with each turn close to adjacent turns. A steep pitch provides few turns with the turns spaced far apart. The height of the thread from the surface of the screw core to the apex of the thread can be deep or shallow. The thickness of the thread can be varied.

Threads have a superior surface on the side facing the screw head and an inferior surface facing the screw tip. The engagement of the superior surface with the bone provides resistance to screw pull-out. The angle between the inferior and superior surfaces is the thread angle. If this angle is small, the thread is narrow as is a knife. If the thread angle is large, then the thread is wide and strong. The need for a knife-like thread to cut through the bone must be balanced against the need for a strong thread.

There are a few references regarding thread shape. U.S. Pat. No. 4,463,753, issued Aug. 7, 1984, entitled "Compression Bone Screw" discloses that the angle made by a thread cross-section is "critical" to the operation of the screw. The angle between the superior and inferior thread surface should be between 30 and 50 degrees, with 40 degrees being optimal according to the '753 Patent. Threads having an angle of less than 20 degrees are weak and can fail if the angle is greater than 60 degrees, the tread will strip out the bone between the treads. Similarly, U.S. Pat. No. 4,870,957, issued Oct. 3, 1989, entitled "Ligament Anchor System" discloses a range of angles for the interior and superior surfaces of the threaded studs that it discloses.

I have found that bone screws can be improved by holding constant the outside screw diameter from thread tip-to-tip and by mounting the helical spread on a tapered screw core. In addition, the screw thread can be further modified by varying the cross-sectional shape of the thread from the tip to the head of a screw. The thickness of the thread near the tip of the screw has a narrow cross-section. The narrow thread and narrow core easily cut into the bone as the screw rotates into the bone. There is minimal tearing and displacement of the bone by the insertion of the narrow thread and pointed core. The thread and core become thicker toward the head of the screw to increase thread strength and to displace bone matter downward against the superior thread surface. Because the core diameter is relatively large at its junction with the screw head, the screw can withstand high torque without having the screw head shear off the core.

The cross-section of the thread and core gradually thicken from the tip to the head of the screw. It is preferable that the thread be thickened by increasing the angle between the inferior thread surface and a line normal to the screw axis. This angle is smallest at the screw tip and widest at the head. The angle of the superior surface is constant along the length of the screw. By thickening the thread, the inferior surface shifts downward toward the adjacent superior surface. By thickening the core, the sidewall of the core gradually moves outward from the bottom of the thread. Accordingly, as the thread rotates into the bone, the inferior thread surface and core sidewall gradually displace the bone matter between the threads down against the adjacent superior thread surface.

The bone matter is compressed against the superior thread surface and partially rotated downward against the superior surface. Compressing bone matter against the superior surface increases the bone resistance to thread pull out. Similarly, rotating bone matter downward aligns the bone matter to enhance the resistance to axial load forces on the screw.

By increasing the thread and core thickness in the direction of the screw head, the thread and core are thickest and strongest near the head. This is particularly advantageous in bones because of the hard cortical bone shell. The cortical bone is harder and more compact than the spongy cancellous matter in the center of bones. The cortical bone provides the bulk of the bone's resistance to screw pull-out forces (axial load forces). The thread and core near the screw head engages the cortical bone and, thus, carry much of the axial load on the screw. The thicker threads of the present invention are optimal for supporting large loads at the cortical bone. Moreover, the varying thickness of the thread compresses and rotates the cortical bone downward against the superior screw surface to provide enhanced pull-out resistance. Also, the thicker core at the head enhances the lateral load to failure strength of the screw. The core is thickest near the: head which is where the greatest lateral compression and distractive forces act on the screw. These forces act to bend the screw just below the head and the thick core near the head provides the greatest resistance to bending.

It is an object of my invention to provide an improved screw for bones, laminated woods, and other materials. In particular, it is an object of my invention to enhance the pull out resistance of screws for bones and other materials. In addition, it is an object of my invention to provide a screw able to withstand large load forces without shearing off the head of the screw or pulling the screw out of its position.

BRIEF DESCRIPTION OF THE DRAWINGS

FIG. 8 is a side cross-sectional view of a second preferred embodiment of the screw invention, and FIG. 9 is a side cross-sectional view of the screw shown in FIG. 8 as inserted in a bone.

DETAILED DESCRIPTION OF THE DRAWINGS

Figure 1:
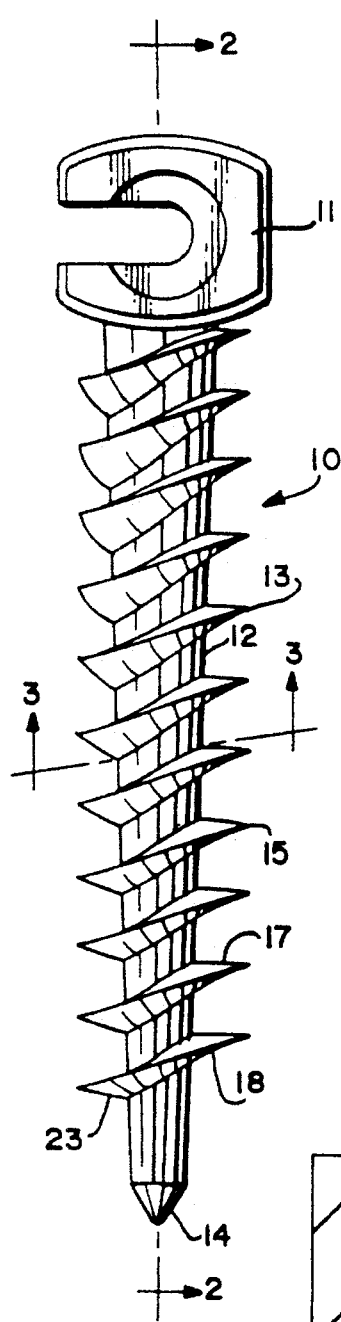
FIG. 1 is a side view of a preferred embodiment of my screw invention.
Figure 3:
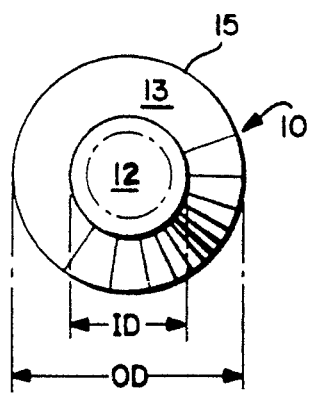
FIG. 3 is an axial cross-section along line 3—3 of FIG. 1.
Figure 2:
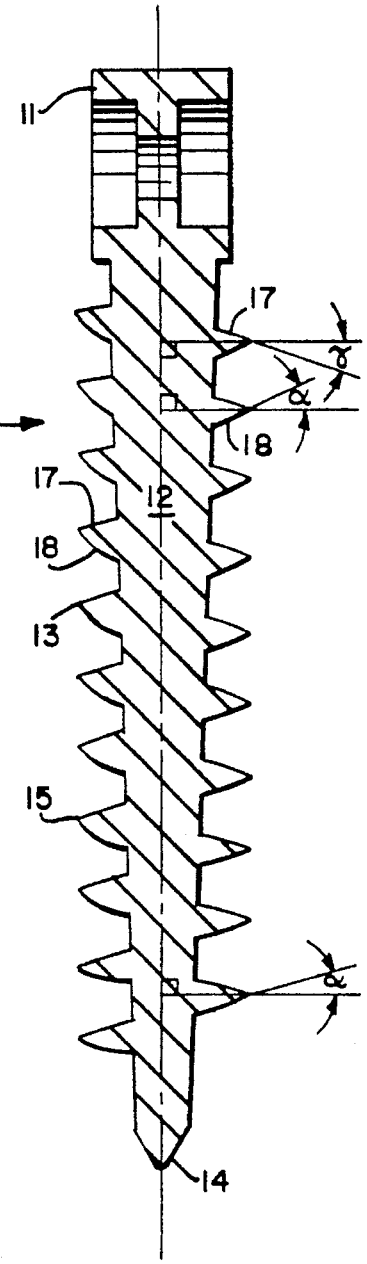
FIG. 2 is a longitudinal cross-sectional view along line 2—2 of FIG. 1.

FIGS. 1 to 3 show the preferred embodiment of the bone screw 10. The screw has a head 11 attached to a core 12 that has a helical screw thread 13. The core is a tapered cylindrical shaft. The core can be solid for enhanced strength or have an axial channel to allow medical devices, e.g., stylet or optical fibers, to pass through the screwy into the bone. The core has a pointed tip 14 at its end opposite to the head. The diameter of the core is smallest at the tip. The diameter gradually increases along the length of the core and the largest diameter is adjacent the screw head.

The diameter of the core is the inside diameter (ID) of the screw. The outside diameter (OD) of the screw is the distance from thread apex 15 through the screw axis to thread apex. In the preferred embodiment, the outside diameter is constant along the length of the screw. However, the OD may be varied in other embodiments.

The depth of the screw thread is the distance between the thread apex 15 and the outer surface of the core. The thread depth is one-half the difference between the outside and inside diameters of the thread. In the preferred embodiment, the thread depth is greatest near the tip 14 and decreases along the length of the screw toward the head 11.

Figure 6:
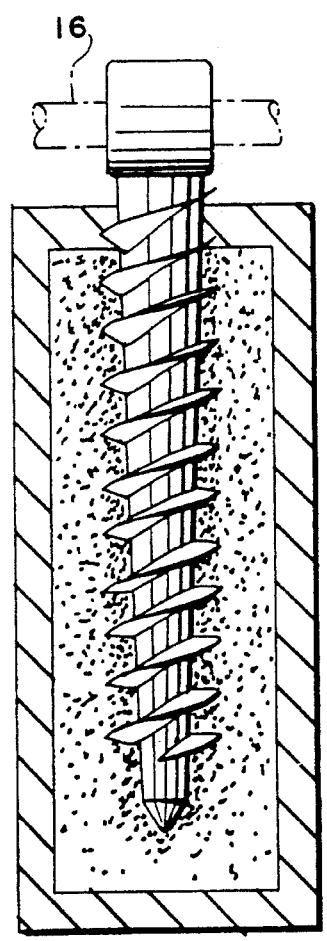

The thread forms a helical spiral around the core. In the preferred. embodiment there is only one thread. Other embodiments may have more than one thread circling the core. The number of threads and thread pitch are parameters that persons of ordinary skill in screw design routinely select. Moreover, these parameters depend on the type of bone or other material in which the screw is to be inserted, and on the purpose of the screw. If the, screw is to anchor a rod 16 (FIG. 6) to support the spine, then the thread pitch and other screw parameters should be selected so that the screw can withstand large shearing and axial loads. If the screw is to be used for other purposes, then other factors will dictate the selection of screw design parameters.

The tread has a superior surface 17 and an inferior surface 18. The superior surface faces the screw head and the inferior surface faces the tip. Both surfaces form a narrow ribbon helix around the core. Both surfaces are continuous along the length of the core. The apex 15 of the screw thread is the ridge formed by the intersection of the superior and inferior surfaces of the thread. In the preferred embodiment, the apex is sharp to cut through the bone.

The superior surface forms an angle gamma ($\gamma$) with a line normal to the axis of the screw. Angle gamma is constant for the entire screw. The superior surface maintains a constant orientation with respect to the axis of the screw.

The inferior surface 18 forms angle alpha ($\alpha$) with a line normal to the screw axis. Angle alpha is small near the tip and large near the screw head. As the inferior surface curls around the core from the tip to the head, angle alpha gradually expands the thickness of the thread. In the preferred embodiment, angle alpha increases linearly. It is contemplated that angle alpha can increase at any suitable rate in other embodiments of the invention.

The screw of this invention can be made using ordinary and well-known screw manufacturing techniques. Persons of ordinary skill in bone screw manufacture are able to make a screw as described in this application with, at most, ordinary and routine experimentation. I am not aware of any optimal or best method to be used to manufacture the screw. The screw can be made of the same bio-compatible materials used to make prior bone screws. I have not found that any one screw material is best suited for my invention.

FIGS. 4 to 7 show the bone screw 10 being inserted into a bone 20 and in operation. The bone has a hard cortical shell 21 and covering a loose, porous cancellous bone 22. The cortical shell is relatively strong but somewhat brittle. The cortical bone is easily cracked and broken by bone, screws. However, the shell provides a substantial portion of the resistance force to the bone screw. The spongy cancellous bone provides some resistance to the screw but can be easily torn.

A pilot hole, with stylet (not shown), is sometimes made by the surgeon in the bone before inserting the bone screw. Inserting the stylet before screw placement allows the surgeon to use radiographic imaging techniques to ensure that the subsequent screw placement will not damage, the bone or nerves when fully inserted. For example, screws inserted into the pedicle of vertebra could, if misplaced, damage the nerves in the spinal cord. Accordingly, a surgeon must be careful to position the screw where it will provide a firm and secure anchor without harming the patient.

Figure 7:
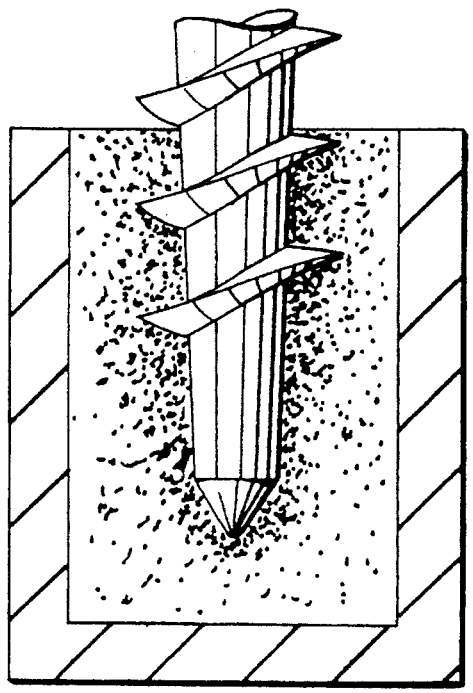
FIG. 7 is an enlarged side view of a screw tip in a bone.
Figure 4:
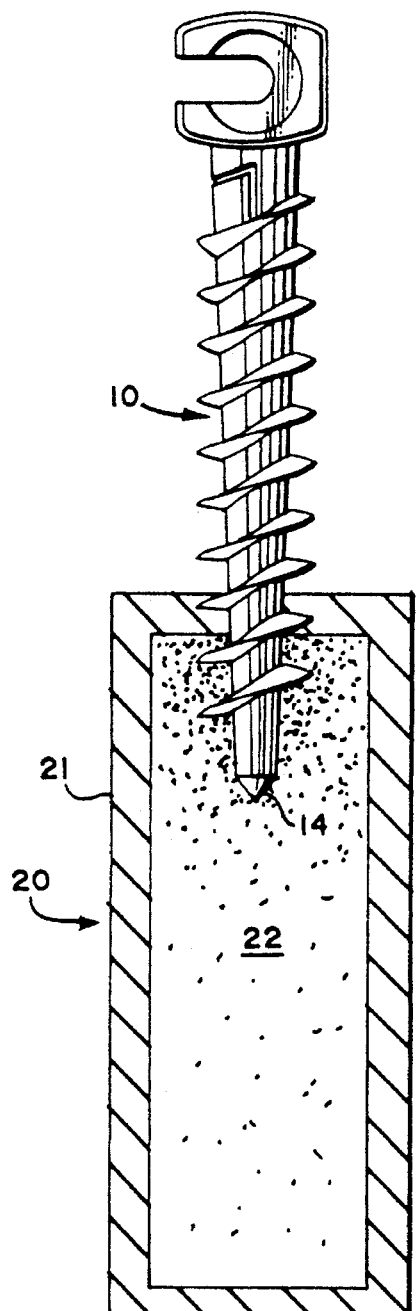
FIGS. 4 to 6 are side views showing a preferred embodiment of my screw invention being threaded into a bone.
Figure 5:
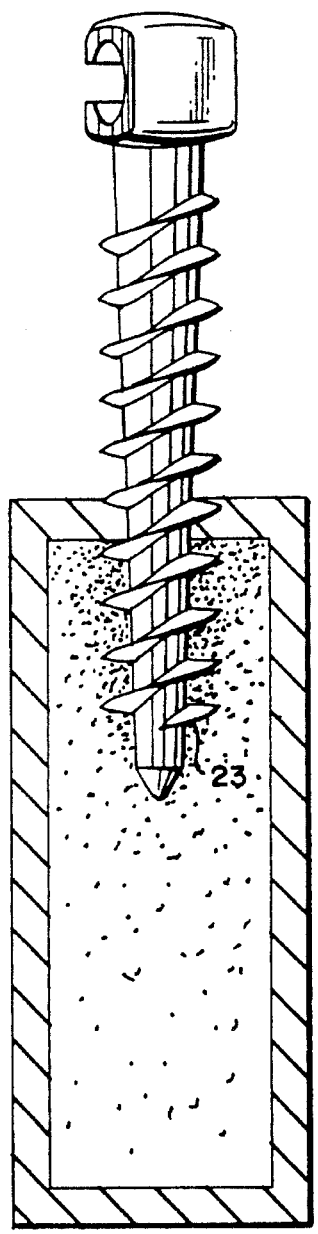

As shown in FIGS. 4 and 7, the cancellous spongy bone 22 is displaced as the tip 14 of the screw passes through the bone. The screw tip is tapered but not sharp to avoid estravication through opposite or laterally positioned conical bone as when the screw is not aligned properly with the bone. The tapered but blunt tip passes through the cortical bone without cracking or damaging the bone. The displaced cancellous bone 22 is pushed slightly downward by the screw tip but remains adjacent the screw. Moreover, the cancellous material does not tear or rip away from the surface of the core or threads.

The leading edge 23 of the thread (FIG. 5) cuts a path in the bone for the thread. The leading edge of the thread is thin and sharp, similar to a knife edge. The thread is thin near the tip because angle alpha is small so that the inferior surface is nearly normal to screw axis. Since the apex of the thread is knife sharp, it easily cuts through the hard cortical bone without cracking the bone. Similarly, the sharp thread cuts through the soft cancellous bone without tearing or ripping the interior of the bone. Accordingly, the leading edge of the thread creates a narrow passageway through the bone for the thread.

As the screw is rotated downward into the bone, the core thickness increases. The core continually pushes the cancellous matter radially outward and, thus, slightly compresses the cancellous matter surrounding the bone and between the threads. Similarly, as the screw thread moves deeper into the bone, the thickness of the thread in the bone gradually increases. As the angle alpha of the inferior surface of the screw thread expands, the cancellous bone matter immediately below the inferior surface is displaced downward against the lower adjacent superior thread surface. This displacement further compacts the cancellous matter between the threads and against the screw.

By displacing bone downward against the superior surface of the screw thread, the bone's resistance to screw pull-out is increased. The hard conical shell is gradually turned downward against the superior surface of the screw as the screw rotates into the bone. This downward deflection of the cortical bone places it in a better orientation to oppose axial pull-out forces on the screw.

In addition, the cortical bone is pinched tightly between opposing inferior and superior thread surfaces. As the screw rotates into the bone, the thread thickens and reduces the volume between the threads. The cortical bone is compressed between the threads besides being turned slightly downward. The pinching of the cortical bone between the thread further increases the resistance of the bone to pull-out and to shear loads. Moreover, the thread and core are thickest and, thus, strongest at the cortical bone. Accordingly, the screw is able to withstand high loads at the cortical bone owing to the fact that the force fulcrum is located just below the head where the core is thickest.

The cancellous bone also provides support for the bone screw. By gradually increasing the thickness of the thread, the passageway in the cancellous bone is gradually displaced without tearing away from the threads. The cancellous bone is displaced by the inferior surface of the thread and pushed down against the superior thread surface. This compresses the cancellous bone between the threads and orients the bone to oppose screw pull-out. The compaction and orientation of the bone improve the support provided by the cancellous bone and, thereby, increase the pull-out resistance of the screw.

A second embodiment of the invention is shown in FIGS. 8 and 9 which show bone screw 40 having a tapered core 42, a constant outside diameter 44 and constant angled-threads 48. In this second embodiment, the angle (Θ) between the superior and inferior surfaces of the thread remains constant along the length of the screw core. It was a total and unexpected surprise to discover that this second embodiment of the screw is better suited for certain vertebra bone applications than is the first embodiment of the screw. The second screw embodiment has achieved surprising results over the first bone screw embodiment and other traditional bone screws when inserted into the pedicle region of vertebras in a spine.

In the first embodiment, the angle (φ) between the thread surfaces film the tip to the head of the screw increases to compress the malleable bone around the thread. This compression of bone matter increases the hoop stress on the bone due to the screw. This increased hoop stress has recently been discovered to over-stress the vertebral pedicle area of a vertebra in some instances causing a condition commonly referred to as a "blow-out" of the pedicle.

The second screw embodiment 40 compresses the surrounding bone to a lesser degree than does the first screw embodiment. The second screw 40 does not compress the surrounding bone by directing the bone material against the superior thread surface by increasing the thread angle along the length of the screw. Instead, the thread angle (Θ)) remains constant along the screw core. The second screw 40 does compress to a lesser degree the surrounding bone as the tapered core 42 pushes the bone material outward as the expanding core moves into the bone. Accordingly, the second screw 40 retains the constant outside thread diameter and tapered core features of the first thread that provide enhanced screw strength and pull-out resistance. But, the second embodiment forgoes the varying screw thread angle to reduce the stresses imparted to the bone.

Each pedicle 50 of a vertebra is an isthmus between the anterior and posterior regions of the vertebral body 52. Because the pedicle is relatively narrow, it is susceptible to being over-stressed by the hoop stresses imparted by bone screws. If these hoop stresses are too great, the pedicle may crack. By slightly reducing the hoop stresses impaired by the bone screw through the use of the second screw embodiment instead of the first embodiment, a surprising new bone screw has been invented that is suitable for use in vertebral pedicle applications.

The second screw embodiment has achieved in testing the surprising result of greater pull-out resistance when inserted into the pedicle area 50 of a vertebra 52 than a traditional bone screw. In addition, the second embodiment when inserted in a vertebral pedicle has been found to apply less hoop stress to the pedicle isthmus than is applied by the first screw embodiment. Because of its lower hoop stress, the second screw embodiment has a relatively large associated safety factor for vertebral pedicle applications.

The tapered core of tile second screw embodiment provides a relatively large diameter junction between the screw head 54 and the top of the core 56. This thick junction allows the screw to withstand the large forces, e.g. axial, that are applied to vertebral bone screws during screw surgery and during a patient rehabilitation prior to fusion of the vertebras. During rehabilitation, extremely large stress can be applied to bone screws, and these stresses have been known to break traditional screws. In bone screws with relatively thin cores, the screw head has sheared off from the, core during loading and in use such that the screw fails. Prior efforts to increase the core diameter have resulted in screws having thick tips that tend to crack the bone surface and "blow-out" the pedicle. The present invention with a tapered core provides a fine screw tip to enter the bone and a thick core where the core joins with the screw head.

The screws described in this application can be customized for particular bone applications. The second screw embodiment is an adaptation of the invention for the vertebral pedicle. The second screw embodiment may be configured to particular pedicle applications. By varying the tip width of the screw and the taper of the core, the screw may be adapted, for example, to a vertebral pedicle having narrow a frontal area and/or sagittal diameter. For example, by varying the taper of the core, the diameter of the screw core adjacent the pedicle may be reduced to minimize the stress imparted to the bone and the diameter of the core near the screw head may be large to provide a strong base tier the screw head.

The invention has been described in what is considered to be the most practical and preferred embodiment. The invention is not limited to the disclosed embodiment, and covers various modifications and equivalent structures included within the spirit and scope of the appended claims.

What is claimed is:

1. A bone screw having a tapered core and a thread having a constant outside diameter, wherein substantially the entire thread has a sharp apex, and said thread has upper and lower surfaces forming in cross-section an acute angle, wherein said angle is substantially constant for the entire thread helix.

2. A bone screw as in claim 1 wherein said thread includes superior and inferior thread surfaces that each form a constant angle to the core.

3. A bone screw as in claim 1 wherein said screw is a vertebral pedicle bone screw.

4. A bone screw comprising:

a conical core having a tip at one end and a wide diameter second end joining with a screw head, and a thread helix attached to said core and curling around the axis of said core, the outside diameter of said helix being substantially uniform along said core, substantially the entire thread helix has a sharp apex, and said thread has upper and lower surfaces forming in cross-section an acute angle, wherein said angle is substantially constant for the entire thread helix.

5. A screw as in claim 4 wherein said thread has inferior and superior surfaces, the orientation of said interior surface with respect to the core being substantially constant.

* * * * *